(12) United States Patent
Lim

(10) Patent No.: US 11,597,650 B2
(45) Date of Patent: Mar. 7, 2023

(54) METHOD FOR PREPARING LITHIUM BIS(FLUOROSULFONYL)IMIDE

(71) Applicants: CLS INC., Seongnam-si (KR); SOLVAY FLUOR GMBH, Hannover (DE)

(72) Inventor: Kwang Min Lim, Yongin-si (KR)

(73) Assignees: CLS INC., Seongnam-si (KR); SOLVAY FLUOR GMBH, Hannover (DE)

( * ) Notice: Subject to any disclaimer, the term of this patent is extended or adjusted under 35 U.S.C. 154(b) by 111 days.

(21) Appl. No.: 15/777,269

(22) PCT Filed: Sep. 28, 2016

(86) PCT No.: PCT/KR2016/010843
§ 371 (c)(1),
(2) Date: May 18, 2018

(87) PCT Pub. No.: WO2017/090877
PCT Pub. Date: Jun. 1, 2017

(65) Prior Publication Data
US 2018/0370799 A1    Dec. 27, 2018

(30) Foreign Application Priority Data

Nov. 26, 2015 (KR) .................. 10-2015-0166565
Sep. 19, 2016 (KR) .................. 10-2016-0119266

(51) Int. Cl.
| | | |
|---|---|---|
| *C01B 21/086* | (2006.01) | |
| *H01M 10/0568* | (2010.01) | |
| *H01M 10/0525* | (2010.01) | |
| *C07C 311/48* | (2006.01) | |
| *C07F 1/02* | (2006.01) | |

(52) U.S. Cl.
CPC .......... *C01B 21/086* (2013.01); *C07C 311/48* (2013.01); *C07F 1/02* (2013.01); *H01M 10/0525* (2013.01); *H01M 10/0568* (2013.01); *H01M 2300/0025* (2013.01)

(58) Field of Classification Search
CPC .................................................. C01B 21/086
See application file for complete search history.

(56) References Cited

U.S. PATENT DOCUMENTS

| | | | | |
|---|---|---|---|---|
| 2012/0041233 A1* | 2/2012 | Sato | ................... | C01B 21/0935 564/154 |
| 2013/0068991 A1* | 3/2013 | Sato | .................... | C01B 21/086 252/62.2 |
| 2013/0323155 A1* | 12/2013 | Tsubokura | ............ | C01B 21/093 423/386 |
| 2013/0331609 A1* | 12/2013 | Tsubokura | .......... | C01B 21/0923 564/82 |
| 2014/0369919 A1* | 12/2014 | Schmidt | ............ | H01M 10/0525 423/386 |
| 2016/0248122 A1* | 8/2016 | Hwang | ............. | H01M 10/0569 |
| 2016/0304347 A1* | 10/2016 | Buisine | ............... | H01M 10/052 |

FOREIGN PATENT DOCUMENTS

| | | |
|---|---|---|
| JP | 2014-162680 A | 9/2014 |
| WO | 2010010613 A1 | 1/2010 |
| WO | 2011/149095 A1 | 12/2011 |

OTHER PUBLICATIONS

H. Nakagawa, "Vacuum Fractionating Apparatus and Molecular Distillation Equipments", Journal of Japan Oil Chemist's Society, 1967, vol. 16, No. 5, pp. 45-52 (9 pages).
Office Action issued in Japanese Application No. 2018-547239, dated Dec. 20, 2020 (25 pages).

* cited by examiner

*Primary Examiner* — Ngoc-Yen Nguyen
(74) *Attorney, Agent, or Firm* — Osha Bergman Watanabe & Burton LLP

(57) ABSTRACT

The present invention relates to a novel method for preparing lithium bis(fluorosulfonyl)imide and, more specifically, to a method for preparing lithium bis(fluorosulfonyl)imide, capable of simply and economically preparing lithium bis (fluorosulfonyl)imide, which is a lithium salt to be used in an electrolyte solution for a lithium secondary battery, in a high yield and with high purity. According to the present invention, the novel method for preparing lithium bis(fluorosulfonyl)imide can resolve the problem of a conventional technique by reacting a bis(chlorosulfonyl)imide compound, which is a starting material, with a fluorination reagent, and then immediately treating the same with an alkali reagent without purification or concentration, and has an effect of enabling lithium bis(fluorosulfonyl)imide to be simply and economically prepared in a high yield and with high purity.

24 Claims, No Drawings

METHOD FOR PREPARING LITHIUM BIS(FLUOROSULFONYL)IMIDE

TECHNICAL FIELD

The present invention relates to a novel method for producing lithium bis(fluorosulfonyl)imide, and more particularly to a method for producing lithium bis(fluorosulfonyl)imide, which is capable of simply and cost-effectively producing lithium bis(fluorosulfonyl)imide, i.e., a lithium salt to be used for an electrolyte for a lithium secondary battery, in high yield and purity.

BACKGROUND ART

In recent years, with the commercialization of various mobile devices, the need for high-performance secondary batteries has increased, and with the commercialization of electric vehicles and hybrid electric motors and the development of electricity storage devices, secondary batteries having characteristics, such as high output, high energy density, high discharge voltage and the like, have been required. In particular, secondary batteries required for electric vehicles should be able to be used over a longer period of time than secondary batteries for small mobile devices, should be able to be charged and discharged within a short time during the use thereof, and should exhibit safety and high output. Therefore, the importance of lithium salts in electrolyte compositions suitable for these secondary batteries has been raised. In particular, it has been found that a lithium bis(fluorosulfonyl)imide compound has excellent required performance compared to $LiPF_6$ and the like.

Meanwhile, the proportion of secondary batteries in the cost structure of electric vehicles approaches 40%, and the proportion of lithium salts in the cost structure of secondary batteries is high. Due to this fact, there has an urgent need to cost-effectively produce high-purity lithium bis(fluorosulfonyl)imide.

A conventional method for producing lithium bis(fluorosulfonyl)imide is represented by the following reaction scheme:

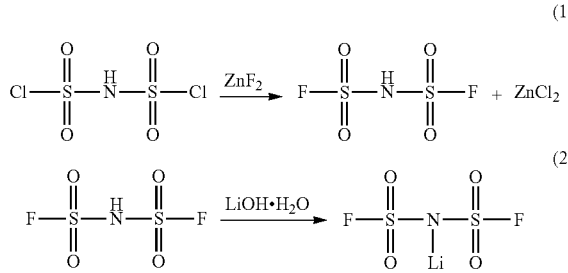

As shown in the reaction scheme above, in step (a) of the conventional production method, bis(chlorosulfonyl)imide as a starting material is reacted with zinc (II) fluoride ($ZnF_2$), thereby producing a bis(fluorosulfonyl)imide compound. Since lithium bis(fluorosulfonyl)imide, a final product obtained in step (2), corresponds to a lithium salt to be used as an electrolyte, metal components other than lithium should be controlled to ppm levels. Thus, removal of the zinc metal component from the reaction product is particularly important. However, the above-described reaction has problems in that expensive zinc (II) fluoride should be used and in that the poorly soluble zinc component should be removed and a large amount of wastewater containing the zinc component is generated. In addition, it has problems in that a portion of bis(fluorosulfonyl)imide is lost, and finally, the zinc metal in lithium bis(fluorosulfonyl)imide should be controlled to ppm levels.

Furthermore, another conventional method for producing lithium bis(fluorosulfonyl)imide is represented by the following reaction scheme:

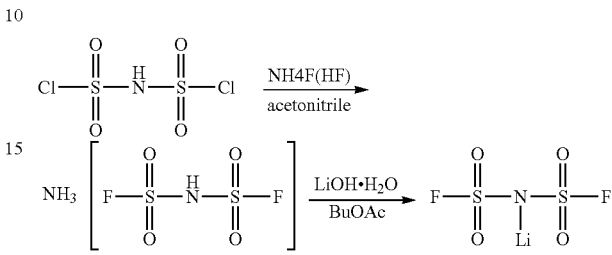

As shown in the reaction scheme above, when bis(chlorosulfonyl)imide as a starting material is reacted with $NH_4F$ $(HF)_n$ (n=1 to 10) which is a fluorinating reagent, ammonium bis(fluorosulfonyl)imide salt is produced as an intermediate product. However, when the reaction is carried out using $NH_4F$ or $NH_4F(HF)_n$ (n=0 to 10) as a fluorinating reagent, $NH_4F$ is merely converted into $NH_4Cl$ and $NH_4F$ $(HF)_n$ merely into $NH_4Cl(HF)_n$, but free-state ammonia ($NH_3$) cannot be released. For this reason, the intermediate product ammonium bis(fluorosulfonyl)imide salt cannot be produced. The reason is because the acidity of bis(fluorosulfonyl)imide ((pH=2 to 3) is lower than that of hydrofluoric acid (HF) or hydrochloric acid (HCl) (pH <0) which is a strong acid, and for this reason, the ammonia functional group cannot be released from $NH_4F(HF)_n$ and $NH_4Cl(HF)_n$ and cannot bind to bis(fluorosulfonyl)imide. Furthermore, the bis(fluorosulfonyl)imide compound is a liquid material having a relatively low boiling point (boiling point 68 to 69° C. at 25 mmHg) and is lost by evaporation during concentration, and thus cannot be obtained in high yield. In addition, $NH_4(HF)_n$ (n=1 to 10) and bis(fluorosulfonyl)imide have a problem in that they may cause corrosion of equipment during the production process due to their strong acidity.

In addition to the above-described methods, there are methods that use an As compound or a Bi compound as a fluorinating reagent or that use anhydrous hydrofluoric acid. However, these methods have problems in that they have to use toxic compounds, or cause corrosion that reduces economic efficiency, and thus are unsuitable in terms of commercial terms.

DISCLOSURE

Technical Problem

The present inventors have investigated a method for producing lithium bis(fluorosulfonyl)imide, and as a result, have found that when a bis(chlorosulfonyl)imide compound as a starting material is reacted with a fluorinating reagent, and then treated with an alkaline reagent directly without purification or concentration, the above-described problems occurring in the prior art can be solved, and lithium bis (fluorosulfonyl)imide can be simply and cost-effectively produced in high yield and purity, thereby completing the present invention.

Therefore, the present invention is intended to provide a novel method for producing lithium bis(fluorosulfonyl)imide.

The present invention is also intended to provide lithium bis(fluorosulfonyl)imide having a purity of 99.9% or higher.

Technical Solution

In order to accomplish the above objects, the present invention provides a method for producing lithium bis(fluorosulfonyl)imide represented by the following Formula 1, the method including the steps of:

(1) reacting bis(chlorosulfonyl)imide with a fluorinating reagent in a solvent, followed by treatment with an alkaline reagent, thereby producing ammonium bis(fluorosulfonyl)imide; and (2) reacting the ammonium bis(fluorosulfonyl)imide with a lithium base:

[Formula 1]

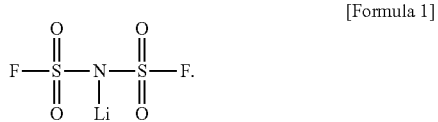

The present invention also provides lithium bis(fluorosulfonyl)imide having a purity of 99.9% or higher, produced by the above-described method.

The novel method for producing lithium bis(fluorosulfonyl)imide according to the present invention is effective in that it can solve the above-described problems occurring in the prior art by reacting a bis(chlorosulfonyl)imide compound as a starting material with a fluorinating reagent, followed by treatment with an alkaline reagent directly without purification or concentration, and can simply and cost-effectively produce lithium bis(fluorosulfonyl)imide in high yield and purity.

BEST MODE

Hereinafter, the present invention will be described in detail.

the present invention provides a method for producing lithium bis(fluorosulfonyl)imide represented by the following Formula 1, the method including the steps of:

(1) reacting bis(chlorosulfonyl)imide with a fluorinating reagent in a solvent, followed by treatment with an alkaline reagent, thereby producing ammonium bis(fluorosulfonyl)imide; and (2) reacting the ammonium bis(fluorosulfonyl)imide with a lithium base:

[Formula 1]

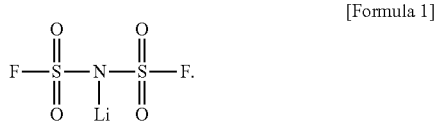

Specifically, the lithium bis(fluorosulfonyl)imide represented by Formula 1 may be produced as shown in the following Reaction Scheme 1:

[Reaction Scheme 1]

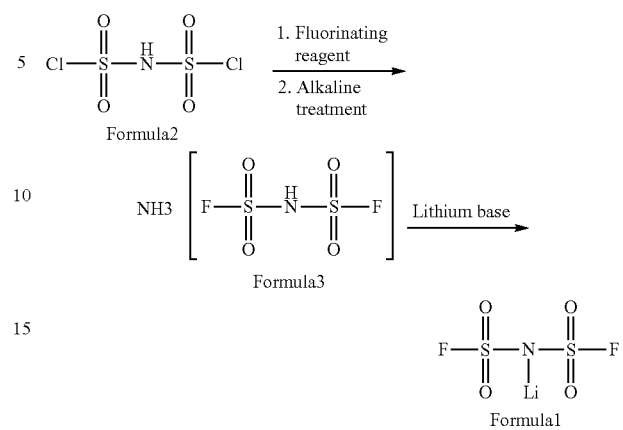

According to Reaction Scheme 1 above, the lithium bis(fluorosulfonyl)imide represented by Formula 1 according to the present invention may be produced by reacting bis(chlorosulfonyl)imide (Formula 2) as a starting material with a fluorinating reagent, followed by treatment with an alkaline reagent without separate concentration and purification, and then adding a lithium base to the resulting intermediate product (Formula 3).

The present invention will now be described in detail.

Step (1) is the step of reacting bis(chlorosulfonyl)imide with a fluorinating reagent in a solvent, followed by treatment with an alkaline reagent, thereby producing ammonium bis(fluorosulfonyl)imide.

The fluorinating reagent is a reagent giving a fluoro group (F) to the reactant, and may be a reagent that produces bis(fluorosulfonyl)imide from the bis(chlorosulfonyl)imide. As the fluorinating reagent, ammonium fluoride ($NH_4F$), hydrogen fluoride (HF), diethylaminosulfur trifluoride, sulfur tetrafluoride or the like may be used. Preferably, ammonium fluoride ($NH_4F$) is used. Most preferably, anhydrous ammonium fluoride is used.

The fluorinating reagent should have a low water content, preferably a water content of 0.01 to 3,000 ppm. When the water content is more than 3,000 ppm, there will be problems in that the fluorinating reagent hydrolyzes the starting material bis(chlorosulfonyl)imide into a sulfuric acid derivative and hydrochloric acid, thus reducing yield, can cause serious equipment corrosion, and further decomposes the starting material or the product under an acidic condition. According to one Comparative Example in the present invention, when commercial ammonium fluoride (water content: about 3%) was used as a fluorinating reagent, it showed problems in that it decomposed the starting material bis(chlorosulfonyl)imide to about 30%, thus reducing yield, and in that the reaction proceeded under a strong acidic condition, and thus additional decomposition of the starting material and the product occurred, resulting in reduced yield, poor color and increased impurities.

The fluorinating reagent is preferably dehydrated by a solvent slurry method. Conventional methods for drying the fluorinating reagent include a method of removing water by heating under vacuum. However, when this method is applied to ammonium fluoride, it has a problem in that the ammonium fluoride may not be sufficiently heated for a long time, because heating of the ammonium fluoride to 100° C. or higher reduces the purity of the product itself. In addition, the use of phosphorus pentoxide ($P_2O_5$), a strong dehydrating agent, is not cost-effective, because a time of 72 hours or more is required to reduce the water content to 3,000 ppm or less. However, when the solvent slurry method of the present invention is used to remove water from the fluorinating reagent, there is an advantage in that the water content can be reduced to 1,000 ppm or less within only several hours.

Solvents that may be used to remove water by the solvent slurry method include alkyl ketones such as acetone, methyl ethyl ketone and methyl isopropyl ketone; alcohols such as methanol, anhydrous ethanol, 1-propanol and isopropanol; alkyl nitriles such as acetonitrile and propionitrile; ethers such as tetrahydrofuran and dialkoxyalkane; and the like. Preferably, the solvent is acetone which is low-priced and enables easy water removal and drying due to its low boiling point. The solvent is preferably used in an amount corresponding to a weight ratio of 0.5 to 1.5 based on the weight of the fluorinating reagent.

The fluorinating reagent may be used in an amount of 2.0 to 10.0 equivalents, preferably 3.0 to 8.0 equivalents, based on the bis(chlorosulfonyl)imide.

The solvent that is used in step (1) may be diethyl ether, diisopropyl ether, methyl t-butyl ether, methyl acetate, ethyl acetate, propyl acetate, butyl acetate, pentane, hexane, heptane or the like, but is not limited thereto. In particular, the solvent should have a low water content, preferably a water content of 0.01 to 100 ppm.

The solvent may be used in an amount of 1.0 to 100.0 equivalents based on the bis(chlorosulfonyl)imide, but is not limited thereto.

The reaction of the bis(chlorosulfonyl)imide (Formula 2) with the fluorinating reagent is performed at an elevated temperature of 30 to 100° C., preferably 50 to 90° C. After bis(fluorosulfonyl)imide is produced by the reaction, it may be treated with an alkaline reagent directly with concentration, filtration and purification, thereby producing ammonium bis(fluorosulfonyl)imide (Formula 3).

As the alkaline reagent, amines such as ammonia, aqueous ammonia solution, alkylamine, arylamine, dialkylamine, diarylamine, alkylarylamine, trialkylamine, dialkylarylamine and alkyldiarylamine; hydroxide, carbonate, bicarbonate, sulfate, alkyl and aryl salts of alkali metals (group I) or alkaline earth metals (group II), and aqueous solutions thereof; and the like may be used. Preferably, hydroxide, carbonate, bicarbonate, sulfate, alkyl and aryl salts of alkali metals (group I) or alkaline earth metals (group II) may be used.

According to Examples of the present invention, treatment with the alkaline reagent (Examples 4-1 to 4-4) showed an increase in lithium bis(fluorosulfonyl)imide yield of 30% or higher compared to when treatment with the alkaline reagent was performed (Comparative Examples 1-1 to 1-2). In particular, the use of salts of alkali metals (group I) or alkaline earth metals (group II) as the reagent showed a high lithium bis(fluorosulfonyl)imide yield of 80% or higher.

Specifically, when the alkaline reagent is used, either the fluorinating reagent (i.e., $NH_4F$) remaining in the reactant or $NH_4Cl$ produced first undergoes an acid-alkali neutralization reaction with the alkaline reagent, thereby generating ammonia. The generated ammonia reacts with bis(fluorosulfonyl)imide, thereby producing ammonium bis(fluorosulfonyl)imide (Formula 3). These reactions are represented by the following Reaction Scheme (2):

[Reaction Scheme 2]

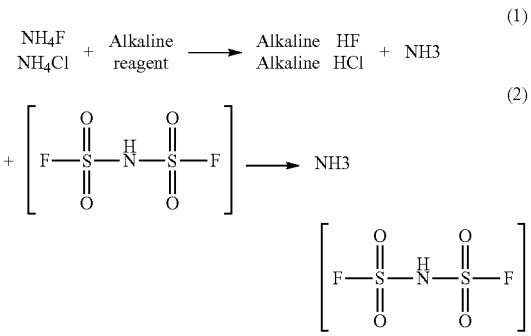

In particular, when the alkaline is used as metal salt powder rather than aqueous solution, there is an advantage in that ammonium bis(fluorosulfonyl)imide (Formula 3) can be prevented from being lost to the aqueous layer, thereby further increasing yield.

In addition, compared to converting bis(fluorosulfonyl)imide directly to a lithium salt, producing lithium bis(fluorosulfonyl)imide (Formula 1) via ammonium bis(fluorosulfonyl)imide (Formula 2) has the following advantages. Since the bis(fluorosulfonyl)imide has a relatively low boiling point (boiling point 68 to 69° C. at 25 mmHg), it is evaporated and lost during transfer or concentration, thus reducing yield. In fact, the bis(fluorosulfonyl)imide compound is a colorless, transparent low-boiling-point liquid. In addition, the bis(fluorosulfonyl)imide is an acidic compound and has problems in that it causes corrosion of the equipment contacting it during reaction or transfer and can cause health problems when workers are exposed thereto. On the other hand, ammonium bis(fluorosulfonyl)imide (Formula 3) is a stable solid compound which is slightly acidic to neutral, causes no equipment corrosion problems and has no risk of evaporation.

Step (2) is the step of reacting the ammonium bis(fluorosulfonyl)imide with a lithium base.

The lithium base used may be lithium hydroxide (LiOH), lithium hydroxide hydrate ($LiOH \cdot H_2O$), lithium carbonate ($Li_2CO_3$), lithium hydrogen carbonate ($LiHCO_3$), lithium chloride (LiCl), lithium acetate ($LiCH_3COO$), lithium oxalate ($Li_2C_2O_4$) or the like, but is not limited thereto.

The lithium base may be used in an amount of 1.0 to 5.0 equivalents based on the ammonium bis(fluorosulfonyl) imide. After addition of the lithium base, the reaction is preferably performed with stirring for 10 to 120 minutes. After the reaction, the aqueous layer may be separated, and lithium bis(fluorosulfonyl)imide which is a final product may be produced through concentration, purification and recrystallization processes. In these processes, the ammonium salt remaining in the reaction product may be removed. The content of the remaining ammonium salt may be 1 to 5000 ppm, preferably 1 to 10 ppm.

In addition, the present invention may include, after step (2), the step of concentrating, purifying and recrystallizing the reaction product.

The concentration may be performed using a molecular distillator at a temperature of 100° C. or lower, preferably 0° C. to 80° C., and a vacuum pressure of 0.1 to 100 Torr. In the concentration, the remaining reaction solvent and the crude concentrate may be present at a weight ratio of 1:0.01 to 1:10.

Through the concentration, purification and recrystallization processes, high-purity lithium bis(fluorosulfonyl)imide may be produced by removing impurities. As a solvent in these processes, dichloromethane, 1,2-dichloroethane, chloroform, carbon tetrachloride, 1,1,2,2-tetrachloroethane, chlorobenzene, dichlorobenzene, trichlorobenzene, diethyl ether, diisopropyl ether, methyl t-butyl ether, pentane, hexane, heptane or the like may be used.

However, in this case, the ratio between the reaction solvent and the recrystallization solvent, crystallization temperature and the like are very important to obtain the product with high purity and in high yield. In a conventional case, lithium bis(fluorosulfonyl)imide is produced only by concentration of a reaction solvent without separate purification. However, in this case, there are problems in that, because impurities are also precipitated, they reduce product qualities such as product purity, color, acidity and the like, and in that the product is not suitable for use as a material for a secondary battery electrolyte. However, the present invention has advantages in that a high-purity crystalline phase which is not a powder phase of the conventional art may be obtained by concentrating the reaction solvent and controlling the ratio between the reaction solvent and the recrystallization solvent, and in that, because the powder has a relatively large particle size and no dust is generated, the powder is suitable for use as a secondary battery electrolyte material having very good workability or flowability.

The reaction solvent is preferably present at a weight ratio of 0.01 to 1.0 relative to the lithium bis(fluorosulfonyl)imide before purification, and the crystallization solvent is present at a weight ratio of 1.0 to 100.0 relative to the lithium bis(fluorosulfonyl)imide before purification. In addition, the recrystallization temperature is preferably between 0 and 80° C., and the recrystallization solvent preferably has a water content of 0.1 to 100 ppm. Through the concentration, purification and recrystallization processes, lithium bis(fluorosulfonyl)imide having a purity of 99.9% or higher may be provided.

In addition, the present invention may provide lithium bis(fluorosulfonyl)imide having a purity of 99.9% or higher by performing additional recrystallization of the concentrated, purified and recrystallized product to remove insoluble components. In this additional recrystallization, alkanes, alcohols, ketones, ethers, esters, carbonates or the like may be used as a recrystallization solvent, and the water content of the solvent is 100 ppm or less.

The present invention has advantages in that it provides lithium bis(fluorosulfonyl)imide having a high purity of at least 99.9%, and provides lithium bis(fluorosulfonyl)imide having an ultra-high purity of at least 99.99% through the concentration, purification and recrystallization processes.

MODE FOR INVENTION

Hereinafter, preferred embodiments of the present invention will be presented in order to facilitate understanding of the present invention. However, the following examples are provided only for the purpose of easier understanding of the present invention, and the scope of the present invention is not limited by the examples.

EXAMPLE 1

Production of Anhydrous Ammonium Fluoride (NH$_4$F)

To a 500-mL flask equipped with a stirrer, a condenser and a thermometer, 100 g of commercial ammonium fluoride (purity: 96%; a water content of 3.6% as measured by Karl Fischer analysis) and 120 g of acetone were added and stirred at room temperature for 3 hours. Then, the acetone slurry of stirred ammonium fluoride was filtered through filter paper, and ammonium fluoride collected on the filter paper was collected in a 250-mL round-bottom flask. Next, the remaining acetone was evaporated under reduced pressure (10 Torr) at 40° C. and dried, thereby obtaining 93 g of anhydrous ammonium fluoride as a white crystal.

The obtained product had a water content of 760 ppm as measured by Karl Fischer analysis and was used in reaction.

EXAMPLE 2

Production of Ammonium Bis(Fluorosulfonyl)Imide 2-1. Use of Anhydrous NH$_4$F/Treatment with Li$_2$CO$_3$ Powder To a 1,000-mL fluororesin container equipped with a stirrer, a condenser and a thermometer, 34.2 g of anhydrous ammonium fluoride and 450 g of butyl acetate (water content: 80 ppm) were added at room temperature under a nitrogen atmosphere. While the mixture was stirred, 50 g of bis(dichlorosulfonyl)imide was added slowly thereto. Next, the mixture was allowed to react while being heated to 80° C., thereby producing bis(fluorosulfonyl)imide.

After completion of the reaction, the temperature was lowered to 60° C., and 17.1 g of Li$_2$CO$_3$ powder was added slowly to the reaction product and allowed to react. Thereafter, the reaction product was cooled to room temperature, and the generated salt was filtered using filter paper. The filtered butyl acetate layer was concentrated under reduced pressure, thereby obtaining white powder. IR analysis and elemental analysis showed that the white powder was ammonium bis(fluorosulfonyl)imide. 43.0 g of the white powder was obtained (yield: 94%; purity: 99.0%).

2-2. Use of Anhydrous NH$_4$F/Treatment with K$_2$CO$_3$ Powder 41.3 g of ammonium bis(fluorosulfonyl)imide was obtained (yield: 90%; purity: 98.0%) according to the same method as described in Example 2-1, except that 32.0 g of K$_2$CO$_3$ was used instead of 17.1 g of the Li$_2$CO$_3$ powder used in Example 2-1.

2-3. Use of Anhydrous NH$_4$F/Treatment with Ammonia Water 38.1 g of ammonium bis(fluorosulfonyl)imide was obtained (yield: 83%; purity: 99.0%) according to the same method as described in Example 2-1, except that 15.8 g of 25% (v/v) ammonia water was used instead of 17.1 g of the Li$_2$CO$_3$ powder used in Example 2-1.

2-4. Use of Anhydrous NH$_4$F/Treatment with Lithium Hydroxide Hydrate 37.1 g of ammonium bis(fluorosulfonyl)imide was obtained (yield: 81%; purity: 99.0%) according to the same method as described in Example 2-1, except that an aqueous solution of 5.5 g of lithium hydroxide hydrate in 28.2 g of distilled water was used instead of 17.1 g of the Li$_2$CO$_3$ powder used in Example 2-1.

EXAMPLE 3

Production of Lithium Bis(Fluorosulfonyl)Imide from Ammonium Bis(Fluorosulfonyl)Imide To a 1,000-mL round-bottom flask equipped with a stirrer, a condenser and a thermometer, 30.0 g of ammonium bis(fluorosulfonyl)imide, obtained in Examples 2-1 to 2-4, and 300 g of butyl acetate, were added at room temperature under a nitrogen atmosphere. The mixture was stirred at room temperature for 30 minutes, and an aqueous solution of lithium hydroxide hydrate ($LiOH \cdot H_2O$) was added thereto in an amount of 2 equivalents, followed by further stirring for 60 minutes.

After completion of the reaction, the reaction product was separated into a butyl acetate layer and an aqueous layer by use of a separatory funnel. The obtained butyl acetate layer was concentrated under reduced pressure at 80° C. or below until the remaining solvent amount reached 5 wt % or less based on the weight of the crude product, thereby obtaining a pale yellow concentrate. To the obtained concentrate, a 3-fold weight of 1,2-dichloroethane was added slowly at 80° C. or below, followed by slow cooling to room temperature. The produced crystal was filtered using filter paper, thereby obtaining 25.2 g of a lithium bis(fluorosulfonyl)imide compound as a white crystal (yield: 89%; purity: 99.9%).

EXAMPLE 4

Production of Bis(Fluorosulfonyl)Imide (In-Situ Process)

4-1. Use of Anhydrous $NH_4F$/Treatment with $Li_2CO_3$ Powder

To a 1,000-mL fluororesin container equipped with a stirrer, a condenser and a thermometer, 34.2 g of anhydrous ammonium fluoride and 450 g of butyl acetate were added at room temperature under a nitrogen atmosphere. While the mixture was stirred, 50 g of bis(dichlorosulfonyl)imide was added slowly thereto. Then, the mixture was allowed to react while being heated to 80° C., thereby producing bis(fluorosulfonyl)imide.

After completion of the reaction, the temperature was lowered to 60° C., and 17.1 g of $Li_2CO_3$ powder was added slowly to the reaction product and allowed to react. Thereafter, the reaction product was cooled to room temperature, and the generated salt was filtered using filter paper. To the filtered reaction product, an aqueous solution of lithium hydroxide hydrate ($LiOH \cdot H_2O$) was added in an amount of 2 equivalents, followed by further stirring for 60 minutes.

After completion of the reaction, the reaction product was separated into a butyl acetate layer and an aqueous layer by use of a separatory funnel. The obtained butyl acetate layer was concentrated under reduced pressure at 80° C. or below until the remaining solvent amount reached 5 wt % or less based on the weight of the crude product, thereby obtaining a pale yellow concentrate. To the obtained concentrate, a 3-fold weight of 1,2-dichloroethane was added at 80° C., followed by slow cooling to room temperature. The produced crystal was filtered using filter paper, thereby obtaining 38.8 g of a lithium bis(fluorosulfonyl)imide compound as a white crystal (yield: 85%; purity: 99.9%).

4-2. Use of Anhydrous $NH_4F$/Treatment with $K_2CO_3$ Powder 37.2 g of lithium bis(fluorosulfonyl)imide was obtained (yield: 81%; purity: 99.8%) according to the same method as described in Example 4-1 above, except that 32.0 g of $K_2CO_3$ powder was used instead of 17.1 g of the $Li_2CO_3$ powder used in Example 4-1.

4-3. Use of Anhydrous $NH_4F$/Treatment with Ammonia Water 33.8 g of lithium bis(fluorosulfonyl)imide was obtained (yield: 74%; purity: 99.9%) according to the same method as described in Example 4-1 above, except that 15.8 g of 25% (v/v) ammonia water was used instead of 17.1 g of the $Li_2CO_3$ powder used in Example 4-1.

4-4. Use of Anhydrous $NH_4F$/Treatment with Lithium Hydroxide Hydrate 33.3 g of lithium bis(fluorosulfonyl)imide was obtained (yield: 73%; purity: 99.9%) according to the same method as described in Example 4-1 above, except that an aqueous solution of 5.5 g of lithium hydroxide hydrate in 28.2 g of distilled water was used instead of 17.1 g of the $Li_2CO_3$ powder used in Example 4-1.

COMPARATIVE EXAMPLE 1

Production of Lithium Bis(Fluorosulfonyl)Imide (Non-Alkaline Treatment)

1-1. Use of Commercial $NH_4F$/Non-Alkaline Treatment

To a 500-mL fluororesin container equipped with a stirrer, a condenser and a thermometer, 8.9 g of commercial ammonium fluoride (water content: 3.6%) and 100 g of acetonitrile were added at room temperature under a nitrogen atmosphere. While the reaction mixture was stirred, 10.7 g of bis(dichlorosulfonyl)imide was added slowly thereto. Then, the reaction mixture was allowed to react under reflux for 4 hours while being heated to 84° C.

After completion of the reaction, the temperature was lowered to room temperature, and the generated salt was filtered using filter paper. The filtered salt was washed with 100 g of acetonitrile and combined with the filtered reaction solution, and then the solvent was removed by distillation and concentration under reduced pressure. To the concentrate, 150 g of butyl acetate was added, and 9.7 g of lithium hydroxide hydrate ($LiOH \cdot H_2O$) and 57.8 g of distilled water were added thereto, followed by stirring at 40° C. for 1 hour. Thereafter, the reaction solution was separated into a butyl acetate and an aqueous layer by use of a separatory funnel, and then the aqueous layer was extracted three times with 80 g of butyl acetate. The obtained butyl acetate layer washed once with 6 g of water and concentrated under reduced pressure, thereby obtaining 3.1 g of brown powder. 9.2 g of dichloromethane was added to the obtained powder, but no crystal was obtained, suggesting that a purified lithium bis(fluorosulfonyl)imide compound could not be obtained.

1-2. Use of Anhydrous $NH_4F$/Non-Alkaline Treatment 4.6 g of pale yellow powder was obtained (yield: 49%; purity: 98.1%) according to the same method as described in Comparative Example 1-1 above, except that 8.9 g of anhydrous ammonium fluoride (water content: 760 ppm) was used instead of 8.9 g of the commercial ammonium fluoride (water content: 3.6%) used in Comparative Example 1-1.

EXAMPLE 5

Comparison of Yields of Lithium Bis(Fluorosulfonyl)Imide Compounds According to Examples 4-1 to 4-4 and Comparative Examples 1-1 to 1-2

The yields of the lithium bis(fluorosulfonyl)imide compounds according to Examples 4-1 to 4-4 and Comparative Examples 1-1 to 1-2 above are shown in Table 1 below.

TABLE 1

| | Fluorinating reagent | Alkaline treatment | Yield (%) of lithium bis(fluorosulfonyl)imide |
|---|---|---|---|
| Example 4-1 | Anhydrous NH$_4$F | Li$_2$CO$_3$ powder | 85 |
| Example 4-2 | Anhydrous NH$_4$F | K$_2$CO$_3$ powder | 81 |
| Example 4-3 | Anhydrous NH$_4$F | Ammonia water | 74 |
| Example 4-4 | Anhydrous NH$_4$F | Lithium hydroxide hydrate | 73 |
| Comparative Example 1-1 | Commercial NH$_4$F | Non-treatment | — |
| Comparative Example 1-2 | Anhydrous NH$_4$F | Non-treatment | 49 |

As shown in Table 1 above, treatment with the alkaline reagent (Examples 4-1 to 4-4) showed an increase in lithium bis(fluorosulfonyl)imide yield of 30% or more compared to non-alkaline treatment (Comparative Examples 1-1 to 1-2). In particular, the use of the alkali metal (group I) or alkaline earth metal (group II) salt as the reagent showed a high lithium bis(fluorosulfonyl)imide yield of 80% or more.

In addition, as shown in Comparative Examples 1-1 to 1-2 above, the use of anhydrous NH$_4$F showed a higher yield of lithium bis(fluorosulfonyl)imide compared to the use of commercial NH$_4$F.

EXAMPLE 6

High-Purity Purification of Lithium Bis(Fluorosulfonyl)Imide

To a 500-mL fluororesin container equipped with a stirrer, a condenser and a thermometer, 30 g of 99.9% pure lithium bis(fluorosulfonyl)imide, obtained in Examples 4-1 to 4-4 above, and 90 g of dimethyl carbonate, were added at room temperature under a nitrogen atmosphere. The reaction mixture was heated to 80° C., thereby dissolving the lithium bis(fluorosulfonyl)imide. The solution was cooled to room temperature and stirred for 1 hour, and then trace amounts of undissolved components were filtered out through filter paper. The dimethyl carbonate solution was concentrated by a molecular distillator under reduced pressure (80 Torr) at 60° C. until the remaining solvent amount reached 5 wt % or less based on the weight of the crude product, thereby obtaining a white, transparent, viscous concentrate.

To the obtained concentrate, 1,2-dichloroethane (water content: 80 ppm) was added slowly at a weight ratio of 3 at 60° C., followed by slow cooling to room temperature. The produced crystal was filtered using filter paper, thereby obtaining 27.6 g of a lithium bis(fluorosulfonyl)imide compound as a white crystal (yield: 92%; purity: 99.99%).

EXAMPLE 7

Production and High-Purity Purification of Lithium Bis(Fluorosulfonyl)Imide To a 1,000-mL fluororesin container equipped with a stirrer, a condenser and a thermometer, 34.2 g of anhydrous ammonium fluoride and 450 g of butyl acetate were added at room temperature under a nitrogen atmosphere. While the reaction mixture was stirred, 50.0 g of bis(dichlorosulfonyl)imide was added slowly thereto. Then, the mixture was allowed to react while being heated to 80° C., thereby producing bis(fluorosulfonyl)imide.

After completion of the reaction, the temperature was lowered to room temperature, and a solution of 13.0 g of potassium hydroxide in 52 g of distilled water was added slowly to the reaction product, followed by stirring for 2 hours. Then, the reaction solution was separated into a butyl acetate layer and an aqueous layer by use of a separatory funnel. To the separated butyl acetate layer, lithium hydroxide hydrate (LiOH.H$_2$O) was added in an amount of 2 equivalents, followed by stirring for 60 minutes. The reaction solution was separated into a butyl acetate layer and an aqueous layer by use of a separatory funnel, and then the obtained butyl acetate layer was concentrated under reduced pressure at 80° C. or below until the remaining solvent amount reached 2 wt % based on the weight of the crude product, thereby obtaining a pale yellow solid.

To the obtained solid, dimethyl carbonate was added at a weight of 3 at room temperature, followed by heating to 80° C. to dissolve the solid. The solution was cooled to room temperature and stirred for 1 hour. Then, trace amounts of undissolved components were filtered out using filter paper, and the dimethyl carbonate solution was concentrated under reduced pressure at 60° C. or below until the remaining solvent amount reached 5 wt % or less based on the weight of the crude product, thereby obtaining a pale yellow concentrate.

To the obtained concentrate, 1,2-dichloroethane was added slowly at a weight ratio of 3 at 60° C. or below, followed by slow cooling to room temperature. The produced crystal was filtered using filter paper, thereby obtaining 29.0 g of a lithium bis(fluorosulfonyl)imide compound as a white crystal (yield: 67%; purity: 99.99%).

The invention claimed is:

1. A method for producing lithium bis(fluorosulfonyl) imide represented by the following Formula 1, the method comprising the steps of:
   (1) reacting bis(chlorosulfonyl)imide with a fluorinating reagent, wherein the fluorinating reagent is ammonium fluoride (NH$_4$F) and has a water content of 0.01 to 3,000 ppm, in a solvent, followed by treatment with an alkaline reagent in the form of a metal salt powder, thereby producing ammonium bis(fluorosulfonyl)imide; and
   (2) reacting the ammonium bis(fluorosulfonyl)imide with a lithium base in a reaction solvent to produce a crude product comprising the lithium bis(fluorosulfonyl)imide of Formula 1:

[Formula 1]

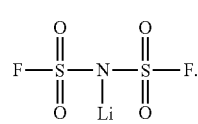

2. The method of claim 1, wherein the fluorinating reagent was dehydrated by a solvent slurry method.

3. The method of claim 2, wherein the solvent is one or more selected from the group consisting of: alkyl ketones, alcohols, alkyl nitriles, and ethers.

4. The method of claim 1, wherein the fluorinating reagent is used in an amount of 2.0 to 10.0 equivalents based on the bis(chlorosulfonyl)imide.

5. The method of claim 1, wherein the solvent is one or more selected from the group consisting of diethyl ether, diisopropyl ether, methyl t-butyl ether, methyl acetate, ethyl acetate, propyl acetate, butyl acetate, pentane, hexane, and heptane.

6. The method of claim 1, wherein the solvent has a water content of 0.01 to 100 ppm.

7. The method of claim 1, wherein the solvent is used in an amount of a weight ratio of 0.5 to 1.5 of the weight of the solvent to the weight of the fluorinating agent.

8. The method of claim 1, wherein the alkaline reagent is one or more selected from the group consisting of: amines, hydroxide, carbonate, bicarbonate, sulfate, alkyl, and aryl salts of alkali metals (group I) or alkaline earth metals (group II), and aqueous solutions thereof.

9. The method of claim 1, wherein the alkaline reagent is one or more selected from the group consisting of: hydroxide, carbonate, bicarbonate, sulfate, alkyl, and aryl salts of alkali metals (group I) or alkaline earth metals (group II).

10. The method of claim 1, wherein the lithium base is one or more selected from the group consisting of: lithium hydroxide (LiOH), lithium hydroxide hydrate (LiOH·H$_2$O), lithium carbonate (Li$_2$ CO$_3$), lithium hydrogen carbonate (LiHCO$_3$), lithium chloride (LiCl), lithium acetate (LiCH$_3$COO), and lithium oxalate (Li$_2$ C$_2$O$_4$).

11. The method of claim 1, wherein the lithium base is used in an amount of 5.0 equivalents based on bis(fluorosulfonyl)imide.

12. The method of claim 1, wherein a content of an ammonium salt remaining in a product of the reaction in step (2) is 1 to 5000 ppm.

13. The method of claim 1, comprising, after step (2), the step of concentrating, purifying and recrystallizing the lithium bis(fluorosulfonyl)imide of the crude product of the reaction in step (2).

14. The method of claim 13, wherein the concentrating is performed using a molecular distillator.

15. The method of claim 13, wherein the concentrating is performed at 0° C. to 80° C.

16. The method of claim 13, wherein the concentrating is performed in a vacuum of 0.1 to 100 Torr.

17. The method of claim 13, wherein the concentrating is performed until a remaining reaction solvent is 5 wt % or less based on the weight of the crude product of the reaction in step (2).

18. The method of claim 13, wherein the purifying is performed using one or more solvents selected from the group consisting of: dichloromethane, 1,2-dichloromethane, chloroform, carbon tetrachloride, 1,1,2,2-tetrachloroethane, chlorobenzene, dichlorobezene, trichlorobenzene, diethyl ether, diisopropyl ether, methyl-t-butyl ether, pentane, hexane, and heptane.

19. The method of claim 13, wherein a solvent for the recrystallizing has a water content of 0.1 to 100 ppm.

20. The method of claim 13, wherein the recrystallizing is performed at a temperature of 0 to 80° C.

21. The method of claim 13, further comprising the step of recrystallizing the concentrated, purified and recrystallized reaction product using a solvent selected from among alkanes, alcohols, ketones, ethers, esters, or carbonates.

22. The method of claim 3, wherein the solvent is one or more selected from the group consisting of: acetone, methyl ethyl ketone, methyl isopropyl ketone, methanol, anhydrous ethanol, 1-propanol, isopropanol, acetonitrile, propionitrile, tetrahydrofuran, and dialkoxyalkane.

23. The method of claim 8, wherein the alkaline reagent is one or more selected from the group consisting of: ammonia, alkylamine, arylamine, dialkylamine, diarylamine, alkylarylamine, trialkylamine, dialkylarylamine, alkyldiarylamine, and aqueous solutions thereof.

24. The method of claim 8, wherein the alkaline reagent is carbonate salt of alkali metal, wherein treatment with an alkaline reagent increases the yield of the lithium bis(fluorosulfonyl)imide compared to no treatment with an alkaline reagent.

* * * * *